United States Patent [19]

Cherpeck

[11] Patent Number: 5,482,523
[45] Date of Patent: Jan. 9, 1996

[54] MANNICH CONDENSATION PRODUCTS OF POLY(OXYALKYLENE) HYDROXYAROMATIC ETHERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 333,458

[22] Filed: Nov. 2, 1994

[51] Int. Cl.$^6$ .............................. C10L 1/22; C07C 69/76; C07C 67/02; C07C 215/00
[52] U.S. Cl. .................. 44/391; 44/399; 44/415; 44/424; 44/425; 554/220; 554/228; 560/105; 560/106; 560/193; 560/254; 564/355; 564/360; 564/361; 564/362
[58] Field of Search .................. 44/391, 399, 415, 44/424, 425; 554/220, 228; 560/105, 106, 193, 254; 564/355, 360, 361, 362

[56] References Cited

U.S. PATENT DOCUMENTS

| | | | |
|---|---|---|---|
| 3,285,855 | 11/1966 | Dexter et al. ........................ | 252/57 |
| 3,849,085 | 11/1974 | Kreuz et al. ........................ | 44/78 |
| 4,134,846 | 1/1979 | Machleder et al. ................ | 252/51.5 A |
| 4,186,102 | 1/1980 | Malec .................................. | 564/355 |
| 4,191,537 | 3/1980 | Lewis et al. ........................ | 44/71 |
| 4,231,759 | 11/1980 | Udelhofen et al. ................ | 44/75 |
| 4,320,021 | 3/1982 | Lange ................................ | 252/51.5 R |
| 4,347,148 | 8/1982 | Davis ................................ | 252/51.5 R |
| 4,859,210 | 8/1989 | Franz et al. ........................ | 44/53 |
| 4,952,732 | 8/1990 | Speranza et al. .................. | 564/390 |
| 5,039,310 | 8/1991 | Blain et al. ........................ | 44/424 |
| 5,196,142 | 3/1993 | Mollet et al. ...................... | 252/311 |
| 5,296,003 | 3/1994 | Cherpeck .......................... | 560/106 |
| 5,399,178 | 3/1995 | Cherpeck .......................... | 44/415 |
| 5,409,507 | 4/1996 | Cherpeck .......................... | 44/399 |

Primary Examiner—Jerry D. Johnson
Attorney, Agent, or Firm—C. J. Caroli

[57] ABSTRACT

Mannich condensation products prepared by the condensation of a compound of the formula:

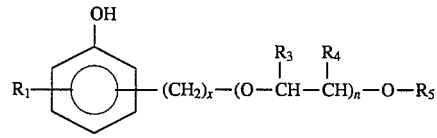

wherein $R_1$ is hydrogen, hydroxy, lower alkyl or lower alkoxy; $R_3$ and $R_4$ are independently hydrogen or lower alkyl; $R_5$ is hydrogen, alkyl, phenyl, aralkyl, alkaryl, or an acyl group of the formula:

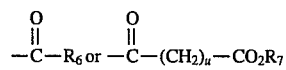

wherein $R_6$ is alkyl, phenyl, aralkyl or alkaryl; $R_7$ is alkyl; u is an integer from 1 to 10; n is an integer from 5 to 100; and x is an integer from 0 to 10;
with an aldehyde and a nitrogen base selected from ammonia, lower alkylamine, a polyamine and mixtures thereof.

The Mannich condensation products and their fuel soluble salts are useful as fuel additives for the prevention and control of engine deposits.

38 Claims, No Drawings

MANNICH CONDENSATION PRODUCTS OF POLY(OXYALKYLENE) HYDROXYAROMATIC ETHERS AND FUEL COMPOSITIONS CONTAINING THE SAME

BACKGROUND OF THE INVENTION

Field of the Invention

This invention relates to Mannich condensation products of certain poly(oxyalkylene) hydroxyaromatic ethers. In a further aspect, this invention relates to the use of such compounds in fuel compositions to prevent and control engine deposits.

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

In addition, U.S. Pat. No. 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3000, (2) an amine, and (3) an aidehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, water repellant agents, paint adhesion promotors, and also as intermediates for preparing surfactants, and pololys finding use in the manufacture of polyurethane foam.

My prior commonly assigned copending U.S. patent Application Ser. No. 07/992,953, filed Dec. 18, 1992, discloses certain poly(oxyalkylene) hydroxyaromatic ethers which provide excellent control of engine deposits, especially intake valve deposits, when employed as fuel additives in fuel compositions. These poly(oxyalkylene) hydroxyaromatic ethers have been found to produce fewer combustion chamber deposits than known aliphatic hydrocarbon-substituted phenolic fuel additives.

SUMMARY OF THE INVENTION

It has now been discovered that certain Mannich condensation products of poly(oxyalkylene) hydroxyaromatic ethers also provide excellent control of engine deposit, including intake valve deposits, with fewer combustion chamber deposit when employed as fuel additives, and further provide excellent control of injector deposits.

More specifically, the compounds of the present invention are Mannich condensation products prepared by the reaction of a poly(oxyalkylene) hydroxyaromatic ether of the formula:

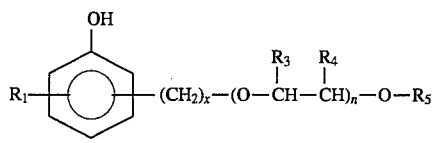

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

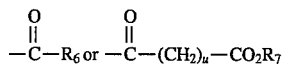

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10;

with an aldehyde having the formula $HR_2C(O)$, wherein $R_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

Fuel soluble salts of the present Mannich condensation products are also contemplated and can be prepared by conventional procedures, for example, by reaction with an appropriate acid or base.

As is frequently the case with Mannich condensation products, the reaction product is typically a mixture of products because of competing or sequential reactions which result in secondary or derivative products, such as cross-linked products.

The amine moiety of the Mannich condensation product is preferably derived from a polyamine having from 2 to about 12 amine nitrogen atoms and from 2 to about 40 carbon atoms. The polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl groups of from 2 to about 10 carbon atoms, and monoketone, monohydroxy, mononitro, monocyano, alkyl and alkoxy derivatives of hydrocarbyl groups of from 1 to 10 carbon atoms. It is preferable that at least one of the basic nitrogen atoms of the polyamine is a primary or secondary amino nitrogen. The polyamine component employed in the present invention has been described and exemplified more fully in U.S. Pat. No. 4,191,537, the disclosure of which is incorporated by reference herein.

The base product and, in general, the principal Mannich condensation product of the invention can be represented by the formula:

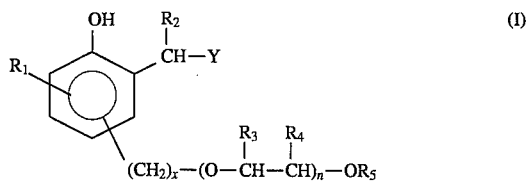

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

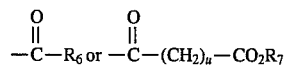

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10;

Y is selected from amino, lower alkylamino having 1 through 6 carbon atoms or a polyamine radical, preferably a polyalkylene polyamine, having 2 through 12 amine nitrogen atoms and 2 through 40 carbon atoms, wherein the attachment of Y to the methylene linking group, i.e., —$CH(R_2)$—, is through one of its amine nitrogen atoms. It is also understood that the —$CHR_2$—Y substituent is ortho to a hydroxy group on the aromatic ring and the remaining substituents may be at any available position on the aromatic ring.

In general, the commercial product will be a mixture of compounds according to formula I because, as noted above, the reaction product will be a mixture of products. In general, there is no commercial reason to isolate individual compounds. If desired, the individual compounds of formula I could be prepared by using individual compounds as starting materials and by isolating individual compounds from the product. But, as noted above, there is normally no commercial reason to isolate particular compounds when the product is used as a fuel additive and it generally would not be economical.

The present invention further provides a fuel composition comprising a major amount of hydrocarbons boiling in the gasoline or diesel range and an effective deposit-controlling amount of a compound or mixture of compounds of the present invention.

The present invention additionally provides a fuel concentrate comprising an inert stable oleophilic organic solvent boiling in the range of from about 150° F. to 400° F. and from about 10 to 70 weight percent of a compound or mixture of compounds of the present invention.

Among other factors, the present invention is based on the discovery that certain Mannich condensation products of poly(oxyalkylene) hydroxyaromatic ethers are surprisingly useful for reducing engine deposits, especially on intake valves, when employed as fuel additives in fuel compositions.

DETAILED DESCRIPTION OF THE INVENTION

As noted above, because of competing or secondary reactions the Mannich condensation product of the present invention is typically a mixture of compounds. For example, where a long chain polyalkylene polyamine reactant is used, although the principal attachment of the polyamine radical to the benzyl ring will occur at the terminal nitrogen atoms, attachment can also occur at an internal amino nitrogen atom. Further, because of competing secondary reactions, cross-linked products are also produced. Thus, for example, in the case where diethylene triamine is the amine reactant, a significant amount of the bis product will also be produced, that is,:

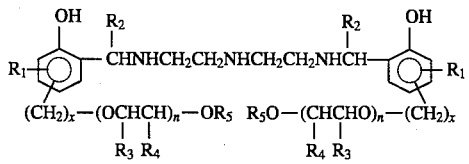

wherein $R_1$, $R_2$, $R_3$, $R_4$, $R_5$, x and n are as defined above.

The polyamine reactant used in the present invention is preferably an acyclic polyamine having terminal amino nitrogen atoms or less preferably a nitrogen heterocycle. In each case the amino nitrogen atoms are separated from each other by at least two carbon atoms. As noted above, the polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl grounds of from 2 to about 10 carbon atoms, and monoketone, monohydroxy, mononitro, monocyano, alkyl and alkoxy derivatives of hydrocarbyl groups of about from 1 to 10 carbon atoms. It is preferable that at least one of the basic nitrogen atoms of the polyamine is a primary or secondary amino nitrogen. The polyamine component employed in the present invention has been described and exemplified more fully in U.S. Pat. No. 4,191,537.

Hydrocarbyl, as used above, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyalkylene amines used in the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxy-isopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, diethyleneoxymethyl, triethyleneoxyethyl, tetraethyleneoxyethyl, diethyleneoxyhexyl, etc. The aforementioned acyl groups are such as propionyl, acetyl, etc. The more preferred substituents are hydrogen, $C_1$–$C_6$ alkyls and $C_1$–$C_6$ hydroxyalkyls.

In the substituted polyalkylene amine, the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

Although, as noted above, a wide range of substituted and unsubstituted polyamines can be used, resulting in the corresponding Mannich condensation product, in general polyalkylene polyamines, including alkylene diamine, and including substituted polyalkyleneamines, e.g., alkyl and hydroxyalkyl-substituted polyalkylene polyamine are preferred. Preferably, the alkyl group linking the amino nitrogen groups contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, 1,3,2-hydroxypropylene, etc. Examples of the polyalkylene amines from which such radicals are derived include ethylene diamine, diethylene triamine, di(trimethylene) triamine, dipropylene triamine, triethylene tetraamine, tripropylene tetraamine, tetraethylene pentamine, and pentaethylene hexamine. Such amines encompass isomers such as branched-chain polyamines and previously mentioned substituted polyamines, including hydroxy- and hydrocarbyl-substituted polyamines. Among the polyalkylene polyamines, those containing 2–12 amino nitrogen atoms and 2–24 carbon atoms are especially preferred, and the $C_2$–$C_3$ alkylene polyamines are most preferred, that is, ethylene diamine, polyethylene polyamine, propylene diamine and polypropylene polyamine, and in particular, the lower polyalkylene polyamines, e.g., ethylene diamine, dipropylene triamine, etc. A particularly preferred polyalkylene polyamine is diethylene triamine.

The amine component of the present fuel additive also may be derived from heterocyclic polyamines, heterocyclic substituted amines and substituted heterocyclic compounds, wherein the heterocycle comprises one or more 5–6 membered rings containing oxygen and/or nitrogen. Such heterocyclic rings may be saturated or unsaturated and substituted with groups selected from the aforementioned substituents. The heterocyclic compounds are exemplified by piperazines, such as 2-methylpiperazine, N-(2-hydroxyethyl)piperazine, 1,2-bis-(N-piperazinyl)ethane and N,N'-bis(N-piperazinyl)piperazine, 2-methyl-imidazoline, 3-amino-piperidine, 3-aminopyridine, N-(3-aminopropyl)morpholine, etc. Among the heterocyclic compounds, the piperazines are preferred.

In terms of deposit control performance and/or manufacturing ease or blending facility, the preferred Mannich condensation products are, referring to the substituents identified in formula I and the corresponding fuel-soluble salts thereof, those having at least one of the following preferred substituents and more preferably two or more.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

Preferably, Y is a radical derived from an unsubstituted polyalkylene polyamine, more preferably polyethylene polyamines or polypropylene polyamines, including ethylene diamine and propylene diamine.

$R_2$ is preferably hydrogen or lower alkyl having 1 to 4 carbon atoms. More preferably, $R_2$ is hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 1 to 24 carbon atoms, or alkylphenyl or phenylalkyl having an alkyl group containing 1 to 24 carbon atoms. More preferably, $R_5$ is hydrogen, alkyl having 4 to 12 carbon atoms or alkylphenyl or phenylalkyl having an alkyl group containing 1 to 12 carbon atoms. Most preferably, $R_5$ is hydrogen or alkylphenyl or phenylalkyl having an alkyl group containing 1 to 12 carbon atoms.

$R_6$ is preferably alkyl having 4 to 12 carbon atoms.

Preferably, n is an integer from 10 to 50. More preferably, n is an integer from 15 to 30. Preferably, x is an integer from 0 to 2. More preferably, x is 0.

A preferred group of Mannich condensation products are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 1 to about 24 carbon atoms or alkylphenyl or phenylalkyl having an alkyl group containing 1 to about 24 carbon atoms; n is 15 to 30 and x is 0; and Y is a polyethylene polyamine radical, including ethylene diamine.

Another preferred group of Mannich condensation products are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 1 to about 24 carbon atoms or alkylphenyl or phenylalkyl having an alkyl group containing 1 to about 24 carbon atoms; n is 15 to 30; x is 1 or 2; and Y is a polyethylene polyamine radical, including ethylene diamine.

A more preferred group of Mannich condensation products are those of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 4 to 12 carbon atoms or alkylphenyl or phenylalkyl having an alkyl group containing 1 to 12 carbon atoms; n is 15 to 30; x is 0; and Y is an ethylene diamine or diethylene triamine radical.

It is especially preferred that the aromatic hydroxyl group or groups present in the compounds of formula I, above, be situated in a meta or para position relative to the poly(oxyalkylene) ether moiety.

Generally, the poly(oxyalkylene) hydroxyaromatic ethers of this invention will contain an average of about 5 to about 100 oxyalkylene units; preferably, 10 to 50 oxyalkylene units; more preferably, 15 to 30 oxyalkylene units.

Preferably, the compounds of the present invention will have a sufficient molecular weight so as to be non-volatile at normal engine intake valve operating temperatures (about 200°–250° C.). Typically, the average molecular weight of the primary or monomeric reaction product, i.e., the compounds of formula I, will range from about 550 to about 6000. More preferably, the compound and salts have an average molecular weight of about from 600 to 4000, more preferably from 700 to 3000. Generally average molecular weight will primarily be a function of the poly(oxyalkylene) ether substituent but can also be influenced by the chain length of the polyamine substituent. The molecular weight of the product mixture will also be affected by cross-linking. Thus, the primary considerations are volatility and fuel solubility and not the technical molecular weight of the product mixture.

Fuel soluble salts of the Mannich condensation products are also useful for preventing or controlling engine deposits and, in some cases, may improve solubility. Suitable salts include, for example, those obtained by protonating the amino moiety with an acid or deprotonating the phenol moiety with a base. Preferred salts are derived from toluenesulfonic acid and methanesulfonic acid or are alkali metal and substituted ammonium salts.

DEFINITIONS

As used herein, the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_a$ wherein $R_a$ is lower alkyl. Typical lower alkoxy groups include methoxy, ethoxy, and the like.

The term "alkaryl" refers to the group:

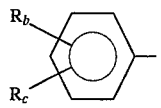

wherein $R_b$ and $R_c$ are each independently hydrogen or an alkyl group, with the proviso that both $R_b$ and $R_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_b$ is alkyl and $R_c$ is hydrogen.

The term "aralkyl" refers to the group:

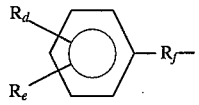

wherein $R_d$ and $R_e$ are each independently hydrogen or an alkyl group; and $R_f$ is an alkylene group. Typical aralkyl groups include, for example, benzyl, methylbenzyl, dimethylbenzyl, phenethyl, and the like.

The term "oxyalkylene unit" refers to an ether moiety having the general formula:

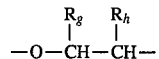

wherein $R_g$ and $R_h$ are each independently hydrogen or lower alkyl groups.

The term "poly(oxyalkylene)" refers to a polymer or oligomer having the general formula:

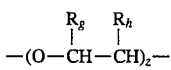

wherein $R_g$ and $R_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

The term "polyamine" as used herein refers to polyamines containing 2 to amine nitrogen atoms and 2 to 40 carbon atoms and includes both acyclic and cyclic polyamines and may be substituted with a variety of substituents so long as the substitution does not significantly adversely affect the deposit control and fuel compatibility properties of the present compositions.

The term "polyalkylene polyamine" by definition contains at least two amine groups.

The term "fuel" refers to liquid hydrocarbon compounds such as petroleum fuels or synthetic fuels which are useful as fuels in spark ignition or combustion fire engines and may also contain minor amounts of other auxiliary fuels.

The term "engine" refers to internal combustion engines and includes both spark ignition engines and combustion fired engines such as diesel engines.

SYNTHESIS

The compounds of formula I can be conveniently prepared by the following schematically represented process:

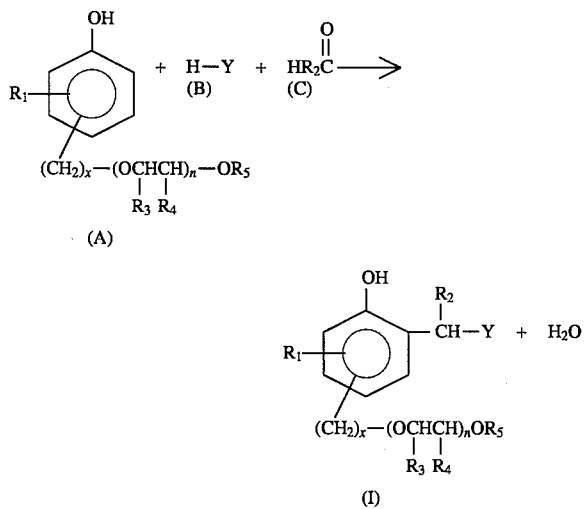

wherein $R_1$, $R_2$, $R_3$, $R_4$, $R_5$, Y, n and x are as defined hereinabove.

This process can be conducted by contacting reactants (A), (B) and (C) under reactive conditions, optionally in an inert solvent or liquid reaction medium. Typically, the reaction is conducted at temperatures in the range of about from 25° C. to 200° C., preferably 75° C. to 150° C. for about from 1 to 50 hours, preferably 5 to 20 hours using mole ratios of reactant in the range of about from 0.1 to 10, preferably 0.3 to 3 moles of reactant (B) and 0.1 to 10, preferably 1 to 5 moles of aldehyde (C) per mole of A.

Suitable inert organic solvents or liquid diluents (reaction medium) which can be used include, for example, toluene, xylene, chloroform, acetonitrile, and the like, and compatible mixtures thereof. Again, although the reaction product is shown for convenience as formula (I) the condensation product will generally be a mixture of products reflecting competing and secondary reaction products; such as, for example, further reactions or cross-linking of amino nitrogens in the polyalkylene amine substituent.

Reactant (B) is the compound form corresponding to the radical Y and includes ammonia, lower alkyl amine (for example, methylamine, isopropylamine, dipropylamine or hexylamine) and polyamines as defined hereinabove. The polyamine must contain at least one primary or secondary amino group because the reaction proceeds by displacement of one of the amino hydrogen groups. Suitable substituted and unsubstituted polyalkylene amines which can be used in the aforedescribed process include, for example, ethylene diamine, 1,2-propylene diamine, 1,3-propylene diamine, diethylene triamine, triethylene tetraamine, hexamethylene diamine, tetraethylene pentamine, dimethylaminopropylene diamine, N-(beta-aminoethyl)piperazine, N-(beta-aminoethyl) morpholine, N,N'-di(beta-aminoethyl)piperazine, N,N'-di(beta-aminoethyl)imidazolidone, N-(beta-cyanoethyl) ethane-1,2-diamine, 1-amino-3,6,9-triazaoctadecane, 1-amino-3,6-diaza-9-oxadecane, N-(beta-aminoethyl) diethanolamine, N'-acetylmethyl-N-(beta-aminoethyl) ethane-1,2-diamine, N-acetonyl-1,2-propanediamine, N-(beta-nitroethyl)-1,3-propane diamine, 1,3-dimethyl-5-(beta-aminoethyl)hexahydrotriazine, N-(beta-aminoethyl)hexahydrotriazine, 5-(beta-aminoethyl)-1,3,5-dioxazine, 2-(2-aminoethylamino)ethanol, and 2-[2-(2-aminoethylamino) ethylamino]ethanol, and the like. Again, because the commercially produced polyalkylene amines are in many instances mixtures of polyalkylene amine, it is convenient to use the commercial mixture and correspondingly the product of formula I will also be a mixture.

The commercial polyalkylamines are typically mixtures in which one or several compounds predominate with the average composition indicated. For example, tetraethylene pentamine prepared by the polymerization of aziridine or the reaction of dichoroethylene and ammonia will have both lower and higher amine members, e.g., triethylene tetraamine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product.

The above-described amines are generally known compounds and, as noted above, are, in many cases, commercial commodities and in any case can be prepared by known procedures or obvious modifications thereof, e.g., substitution of appropriate starting materials and optimization of reaction conditions.

Methods of preparation of amines and their reactions are detailed in Sidgewick's "The Organic Chemistry of Nitrogen", Clarendon Press, Oxford, 1966; Noller's "Chemistry of Organic Compounds" Saunders Philadelphia, 2nd Ed., 1957; and Kirk-Othmer's "Encyclopedia of Chemical Technology" 2nd Ed., especially Volume 2, pp. 99–116.

The compounds of formula A, above, may be prepared by the procedures described in my commonly assigned copending U.S. Patent application Ser. No. 07/992,953, filed Dec.

18, 1992, the disclosure of which is hereby incorporated by reference herein in its entirety.

In accordance with the procedures described in U.S. Ser. No. 07/992,953, the poly(oxyalkylene) hydroxyaromatic ethers of formula A may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(oxyalkylene) hydroxyaromatic ethers of formula A may be prepared from a hydroxyaromatic compound having the formula:

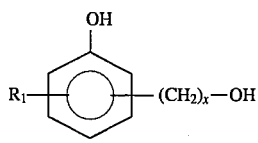

(III)

wherein $R_1$ and x are as defined above.

The hydroxyaromatic compounds of formula III are either known compounds or can be prepared from known compounds by conventional procedures. Suitable hydroxyaromatic compounds for use as starting materials in this invention include catechol, resorcinol, hydroquinone, 1,2,3-trihydroxybenzene (pyrogallol), 1,2,4-trihydroxybenzene (hydroquinol), 1,3,5-trihydroxybenzene (phloroglucinol), 1,4-dihydroxy-2-methylbenzene, 1,3-dihydroxy-5-methylbenzene, 2-t-butyl-1,4-dihydroxybenzene, 2,6-di-t-butyl-1,4-dihydroxybenzene, 1,4-dihydroxy-2-methoxybenzene, 1,3-dihydroxy-5-methoxybenzene, 4-hydroxybenzyl alcohol, 4-hydroxyphenethyl alcohol, and the like.

In a preferred method of synthesizing the poly(oxyalkylene) hydroxyaromatic ethers employed in the present invention, a hydroxyaromatic compound of formula III is first selectively protected to provide a compound having the formula:

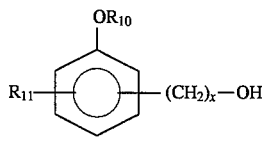

(IV)

wherein $R_{10}$ is a suitable hydroxyl protecting group, such as benzyl, tert-butyldimethylsilyl, methoxymethyl, and the like; $R_{11}$ is hydrogen, lower alkyl, lower alkoxy, or the group $-OR_{13}$, wherein $R_{13}$ is a suitable hydroxyl protecting group, such as benzyl, tert-butyldimethylsilyl, methoxymethyl, and the like. Preferably, $R_{10}$ and $R_{13}$ are benzyl; except in the case where x is 1, then $R_{10}$ and $R_{13}$ are preferably a tert-butyl-dimethylsilyl group.

Selective protection of III may be accomplished using conventional procedures. The choice of a suitable protecting group for a particular hydroxyaromatic compound will be apparent to those skilled in the art. Various protecting groups, and their introduction and removal, are described, for example, in T. W. Greene and P. G. M. Wuts, Protective Groups in Organic Synthesis, Second Edition, Wiley, New York, 1991, and references cited therein. Alternatively, the protected derivatives IV can be prepared from known starting materials other than the hydroxyaromatic compounds of formula III by conventional procedures. In some cases, the protected derivatives IV are commercially available, e.g., 4-benzyloxyphenol is commercially available from Aldrich Chemical Co., Milwaukee, Wis. 53233.

The protected hydroxyaromatic compound of formula IV is then deprotonated with a suitable base to provide a metal salt having the formula:

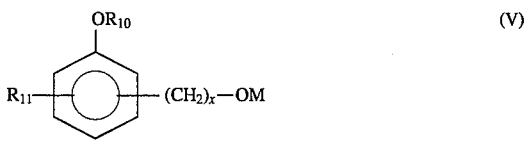

(V)

wherein $R_{10}$, $R_{11}$ and x are as defined above; and M is a metal cation, such as lithium, sodium or potassium.

Generally, this deprotonation reaction will be effected by contacting IV with a strong base, such as sodium hydride, potassium hydride, sodium amide and the like, in an inert solvent, such as toluene, xylene and the like, under substantially anhydrous conditions at a temperature in the range from about −10° C. to about 120° C. for about 0.25 to about 3 hours.

Metal salt V is generally not isolated, but is reacted in situ with about 5 to about 100 molar equivalents of an alkylene oxide (an epoxide) having the formula:

(VI)

wherein $R_3$ and $R_4$ are as defined above, to provide, after neutralization, a poly(oxyalkylene) polymer or oligomer having the formula:

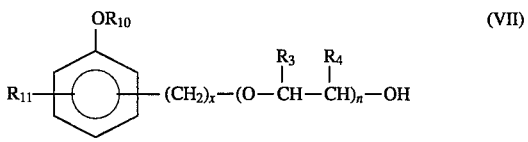

(VII)

wherein $R_3$, $R_4$, $R_{10}$, $R_{11}$, n and x are as defined above.

Typically, this polymerization reaction is conducted in a substantially anhydrous inert solvent at a temperature of about 30° C. to about 150° C. for about 2 to about 120 hours. Suitable solvents for this reaction, include toluene, xylene and the like. The reaction will generally be conducted at a pressure sufficient to contain the reactants and the solvent, preferably at atmospheric or ambient pressure. More detailed reaction conditions for preparing poly(oxyalkylene) compounds may be found in U.S. Pat. Nos. 2,782,240 and 2,841,479, which are incorporated herein by reference.

The amount of alkylene oxide employed in this reaction will depend on the number of oxyalkylene units desired in the product. Typically, the molar ratio of alkylene oxide VI to metal salt V will range from about 5:1 to about 100:1; preferably, from 10:1 to 50:1, more preferably from 15:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides; and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene). However, copolymers are equally satisfactory and random copolymers are readily prepared by contacting the metal salt V with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt V with first one alkylene oxide, then others in any order, or repetitively, under polymerization conditions.

Poly(oxyalkylene) polymers of formula VII may also be 31 prepared by living or immortal polymerization as described by S. Inoue and T. Aida in Encyclopedia of Polymer Science and Engineering, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

Deprotection of the aromatic hydroxyl group(s) of VII using conventional procedures provides poly(oxyalkylene) hydroxyaromatic ethers for use in the present invention having the formula:

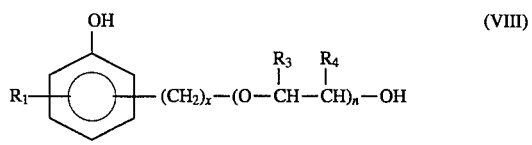

(VIII)

wherein $R_1$, $R_3$, $R_4$, n and x are as defined above.

Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction will be conducted in an inert solvent, preferably a mixture of ethyl acetate and acetic acid, at a temperature of from about 0° C. to about 40° C. for about 1 to about 24 hours.

The poly(oxyalkylene) hydroxyaromatic ethers employed in the present invention containing an alkyl or aralkyl ether moiety, i.e., those having the formula:

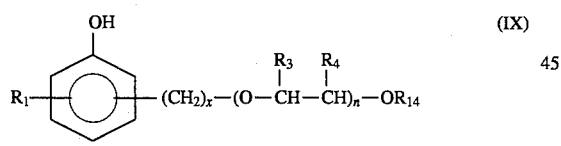

(IX)

wherein $R_1$, $R_3$, $R_4$, n and x are as defined above, and $R_{14}$ is an alkyl group or aralkyl group, may be conveniently prepared from a compound of formula VIII by selectively alkylating the hydroxyl group of the poly(oxyalkylene) moiety of VIII with a suitable alkylating agent.

Typically, this alkylation reaction will be conducted by first contacting VIII with a sufficient amount of a strong base capable of abstracting a proton from each the hydroxyl groups present in VIII, including the aromatic hydroxyl group(s) and the hydroxyl group of the poly(oxyalkylene) moiety. Suitable bases for this reaction include, for example, sodium hydride, potassium hydride, sodium amide and the like. Generally, this deprotonation reaction will be conducted in an inert solvent, such as toluene, tetrahydrofuran, and the like, under substantially anhydrous conditions at a temperature in the range from −10° C. to 120° C. for about 0.25 to about 3 hours. The resulting metal salt is then contacted with about 0.90 to about 1.1 molar equivalents of a suitable alkylating agent at a temperature in the range from 0° C. to 120° C. for about 1 to about 50 hours to afford, after neutralization, a poly(oxyalkylene) hydroxyaromatic ether of formula IX.

Suitable alkylating agents for use in this reaction include alkyl and aralkyl halides, such as alkyl chlorides, bromides and iodides and aralkyl chlorides, bromides and iodides; and alkyl and aralkyl sulfonates, such as alkyl mesylates and tosylates, and aralkyl mesylates and tosylates.

Preferred alkylating agents are primary and secondary alkyl halides having 1 to 30 carbon atoms, and primary and secondary aralkyl halides having 7 to 36 carbon atoms; more preferred alkylating agents are primary alkyl halides having 4 to 12 carbon atoms.

Representative examples of alkylating agents include, but are not limited to, methyl iodide, ethyl iodide, n-propyl bromide, n-butyl bromide, n-pentyl bromide, n-hexyl chloride, n-octyl chloride, n-decyl chloride, benzyl chloride, and phenethyl chloride. Particularly preferred alkylating agents are benzyl chloride and n-butyl bromide.

Alternatively, poly(oxyalkylene) hydroxyaromatic ethers of formula IX may be prepared by alkylating the hydroxyl group of the poly(oxyalkylene) moiety of protected intermediate VII, and then deprotecting the resulting product. The conditions for alkylating intermediate VII are essentially the same as those described above; however, a lesser amount of base will be required since the aromatic hydroxyl groups of VII are in a protected form.

Other suitable methods for preparing alkyl and alkaryl ethers from alcohols, and appropriate reaction conditions for such reactions, can be found, for example, in I. T. Harrison and S. Harrison, Compendium of Organic Synthetic Methods, Vol. 1, pp. 310–312, Wiley-Interscience, New York (1971) and references cited therein.

The poly(oxyalkylene) hydroxyaromatic ethers employed in the present invention containing a phenyl or alkaryl ether moiety, i.e., those having the formula:

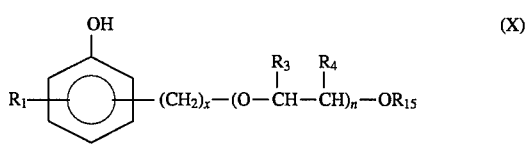

(X)

wherein $R_1$, $R_3$, $R_4$, n and x are as defined above, and $R_{15}$ is a phenyl or alkaryl group, may be prepared from intermediate VII in several steps by first converting the hydroxyl group present on the poly(oxyalkylene) moiety of VII into a suitable leaving group, i.e., forming an intermediate having the formula:

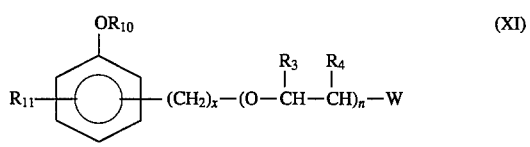

(XI)

wherein $R_3$, $R_4$, $R_{10}$, $R_{11}$, n and x are as defined above, and W is a suitable leaving group; and then displacing the leaving group of XI with a metal salt of a phenol having the formula:

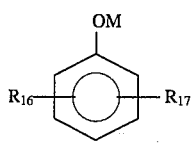

(XII)

wherein $R_{16}$ and $R_{17}$ are each independently hydrogen or an alkyl group. Subsequent deprotection of the resulting product affords poly(oxyalkylene) hydroxyaromatic ethers of formula X.

The hydroxyl group of the poly(oxyalkylene) moiety of VII may be converted into a suitable leaving group by contacting VII with a sulfonyl chloride to form a sulfonate ester, such as a methanesulfonate (mesylate) or a toluenesulfonate (tosylate). Typically, this reaction is conducted in the presence of a suitable amine, such as triethylamine or pyridine, in an inert solvent, such as dichloromethane, at a temperature in the range of about $-10°$ C. to about $30°$ C.

Alternatively, the hydroxyl group of the poly(oxyalkylene) moiety of VII can be exchanged for a halide, such chloride or bromide, by contacting VII with a halogenating agent, such as thionyl chloride, oxalyl chloride or phosphorus tribromide. Other suitable methods for preparing sulfonates and halides from alcohols, and appropriate reaction conditions for such reactions, can be found, for example, in I. T. Harrison and S. Harrison, Compendium of Organic Synthetic Methods, Vol. 1, pp. 331–337, Wiley-Interscience, New York (1971) and references cited therein.

After forming intermediate XI, the leaving group may be displaced therefrom by contacting XI with metal salt XII. Generally, this reaction will be conducted in an inert solvent, such as toluene, tetrahydrofuran and the like, under substantially anhydrous conditions at a temperature in the range of about $25°$ C. to about $150°$ C. for about 1 to about 48 hours. The metal salt XII can be formed by contacting the corresponding phenol with a strong base capable of abstracting the proton from the phenolic hydroxyl group, such as sodium hydride, potassium hydride, sodium amide and the like, in an inert solvent.

Suitable phenolic compounds for use in this reaction include phenol, monoalkyl-substituted phenols and dialkyl-substituted phenols. Monoalkyl-substituted phenols are preferred, especially monoalkylphenols having an alkyl substituent in the para position. Representative examples of suitable phenolic compounds include, but are not limited to, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are those derived from alkylation of phenol with polymers or oligomers of $C_3$ to $C_6$ olefins, such as polypropylene or polybutene. These polymers preferably contain 10 to 30 carbon atoms. An especially preferred alkylphenol is prepared by alkylating phenol with a propylene polymer having an average of 4 units. This polymer has the common name of propylene tetramer and is commercially available.

Alternatively, the poly(oxyalkylene) hydroxyaromatic ethers of formula X can be prepared by displacing a leaving group from an intermediate having the formula:

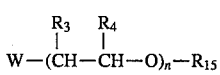

(XIII)

wherein $R_3$, $R_4$, $R_{15}$ and n are as defined above, and W is a suitable leaving group, with metal salt V; and then deprotecting the resulting product. Conditions for this reaction are essentially the same as those described above for reaction of XI with XII. Compounds of formula XIII may be prepared from XII and VI using the conditions described above for the preparation of VII, followed by conversion of the hydroxyl group of the poly(oxyalkylene) moiety of the resulting product into a suitable leaving using the procedures described above for the preparation of XI.

The poly(oxyalkylene) hydroxyaromatic ethers employed in the present invention containing an acyl moiety, i.e., those having the formula:

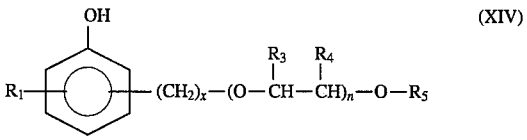

(XIV)

wherein $R_1$, $R_3$, $R_4$, n and x are as defined above; and $R_5$ is an acyl group having the formula:

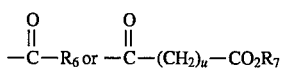

wherein $R_6$, $R_7$ and u are as defined above; may be prepared from intermediate VII by first acylating the hydroxyl group of the poly(oxyalkylene) moiety of VII to form an ester. Subsequent deprotection of the aromatic hydroxyl group(s) of the resulting ester using conventional procedures then affords poly(oxyalkylene) hydroxyaromatic ethers of formula XIV.

Generally, the acylation reaction will be conducted by contacting intermediate VII with about 0.95 to about 1.2 molar equivalents of a suitable acylating agent. Suitable acylating agents for use in this reaction include acyl halides, such as acyl chlorides and bromides; and carboxylic acid anhydrides. Preferred acylating agents are those having the formula: $R_6C(O)$—X, wherein $R_6$ is alkyl having 1 to 30 carbon atom, phenyl, or aralkyl or alkaryl having 7 to 36 carbon atoms, and X is chloro or bromo. More preferred acylating agents are those having the formula: $R_8C(O)$—X, wherein $R_8$ is alkyl having 4 to 12 carbon atoms. Representative examples of suitable acylating agents include, but are not limited to, acetyl chloride, acetic anhydride, propionyl chloride, butanoyl chloride, pivaloyl chloride, octanoyl chloride, decanoyl chloride, 4-t-butylbenzoyl chloride, and the like.

Generally, this reaction is conducted in an inert solvent, such as toluene, dichloromethane, diethyl ether and the like, at a temperature in the range of about $25°$ C. to about $150°$ C. and is generally complete in about 0 5 to about 48 hours. When an acyl halide is employed as the acylating agent, this reaction is preferably conducted in the presence of a sufficient amount of an amine capable of neutralizing the acid generated during the reaction, such as triethylamine, di(isopropyl)ethylamine, pyridine or 4-dimethylaminopyridine.

Another preferred group of acylating agents are the acyl halides having the formula:

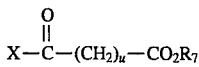
$$X-\overset{O}{\underset{\|}{C}}-(CH_2)_u-CO_2R_7 \quad (XV)$$

wherein $R_7$ is alkyl having 1 to about 10 carbon atoms, u is an integer from 1 to 10, and x is a halogen, preferably chloro or bromo.

The acyl halide of formula XV will generally be derived from a corresponding carboxylic acid having the formula:

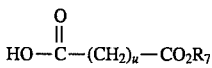
$$HO-\overset{O}{\underset{\|}{C}}-(CH_2)_u-CO_2R_7 \quad (XVI)$$

wherein $R_7$ and u are as defined above, by contacting the carboxylic acid of formula XVI with an inorganic acid halide, such as thionyl chloride, phosphorous trichloride, phosphorous tribromide or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C., for about 1 to about 48 hours. A catalyst, such as N, N-dimethylformamide, may also be used in this reaction.

Suitable carboxylic acids of formula XVI include the mono-alkyl esters of malonic acid, succinic acid, glutaric acid, adipic acid, pimelic acid, suberic acid, azelaic acid and sebacic acid. Representative examples of such compounds include malonic acid mono-methyl ester, succinic acid mono-ethyl ester, adipic acid mono-methyl ester, pimelic acid mono-n-butyl ester and the like. The mono-alkyl esters of these dicarboxylic acids are commercially available or may be prepared by known procedures, e.g., adipic acid mono-methyl ester and mono-ethyl ester are commercially available from Aldrich Chemical Co., Milwaukee, Wis. 53233.

Additional methods for preparing ethers from alcohols, and suitable reaction conditions for such reactions, can be found, for example, in I. T. Harrison and S. Harrison, Compendium of Organic Synthetic Methods, Vol. 1, pp. 273–276 and 280–283, Wiley-Interscience, New York (1971) and references cited therein.

Those skilled in the art will recognize that it may be necessary to block or protect certain functional groups while conducting the present synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, Protective Groups in Organic Synthesis, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art.

The products or product mixtures can be recovered from the respective reaction product mixtures by any suitable separation and purification procedure, such as, for example, extraction, evaporation, and recrystallization. Suitable separation and purification procedures for recovering product mixtures are, for example, illustrated in the Examples set forth hereinbelow.

Fuel Compositions

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the Mannich condensation products of this invention in hydrocarbon fuel will range from about 50 to about 2500 parts per million (ppm) by weight, preferably from 75 to 1000 ppm. When other deposit control additives are present, a lesser amount of the present additive may be used.

The Mannich condensation products of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present. The gasoline fuels may also contain amounts of other fuels such as, for example, methanol.

In diesel fuels, other well-known additives can be employed, such as pour point depressants, flow improvers, cetane improvers, and the like. The diesel fuels can also include other fuels such as, for example, methanol.

A fuel-soluble, nonvolatile carrier fluid or oil may also be used with the Mannich condensation products of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively. These carrier fluids are believed to act as a carrier for the fuel additives of the present invention and to assist in removing and retarding deposits. The carrier fluid may also exhibit synergistic deposit control properties when used in combination with a Mannich condensation product of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

A further understanding of the invention can be had in the following nonlimiting Examples. Unless expressly stated to the contrary, all temperatures and temperature ranges refer to the Centigrade system and the term "ambient" or "room temperature" refers to about 20° C.–25° C. The term "percent" or %" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

The following examples are presented to illustrate specific embodiments of the present invention and synthetic preparations thereof; and should not be interpreted as limitations upon the scope of the invention.

Example 1

Preparation of
α-(4-Benzyloxyphenyl)-ω-hydroxypoly(oxybutylene)

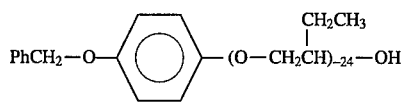

To a flask equipped with a magnetic stirrer, thermometer, addition funnel, reflux condenser and nitrogen inlet was added 6.88 grams of a 35 wt. % dispersion of potassium hydride in mineral oil. Forty grams of 4-benzyloxyphenol dissolved in 500 mL of anhydrous toluene was added dropwise and the resulting mixture was stirred at room temperature for ten minutes. The temperature of the reaction mixture, a thick white suspension, was raised to 90° C. and 430.8 mL of 1,2-epoxybutane was added dropwise. The reaction mixture was refluxed until the pot temperature reached 110° C. (approximately 48 hours) at which time the reaction mixture was a light brown clear solution. The reaction was cooled to room temperature, quenched with 50 mL of methanol and diluted with 1 liter of diethyl ether. The resulting mixture was washed with saturated aqueous ammonium chloride, followed by water and saturated aqueous sodium chloride. The organic layer was dried over anhydrous magnesium sulfate, filtered and the solvents removed in vacuo to yield 390 grams of a yellow oil. The oil was chromatographed on silica gel, eluting with hexane: diethyl ether (1:1), to yield 339.3 grams of the desired product as a colorless oil.

Example 2

Preparation of
α-(4-Hydroxyphenyl)-ω-hydroxypoly(oxybutylene)

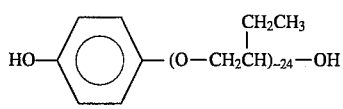

A solution of 54.10 grams of the product from Example 1 in 100 mL of ethyl acetate and 100 mL of acetic acid containing 5.86 grams of 10% palladium on charcoal was hydrogenolyzed at 35–40 psi for 16 hours on a Parr low-pressure hydrogenator. Catalyst filtration and removal of solvent in vacuo followed by azeotropic removal of residual acetic acid with toluene under vacuum yielded 48.1 grams of the desired product as a colorless oil. The product had an average of 24 oxybutylene units. $^1$H NMR (CDCl$_3$) δ 7.2 (broad s, 2H), 6.7 (s, 4H), 3.1–4.0 (m, 72H), 1.2–1.8 (m, 48H), 0.8 (t, 72H).

Similarly, by using the above procedures and the appropriate starting materials and reagents, the following compounds can by prepared:

α-(2-hydroxyphenyl)-ω-hydroxypoly(oxybutylene);

α-(3-hydroxyphenyl)-ω-hydroxypoly(oxybutylene);

α-(3-t-butyl-4-hydroxyphenyl)-ω-hydroxypoly(oxybutylene);

α-(4-hydroxy-3-methoxyphenyl)-ω-hydroxypoly(oxybutylene);

α-(3,4-dihydroxyphenyl)-ω-hydroxypoly(oxybutylene);

α-(3,4-hydroxy-5-methylphenyl)-ω-hydroxypoly(oxybutylene);

α-(3,5-di-t-butyl-4-hydroxyphenyl)-ω-hydroxypoly(oxybutylene); and α-(3,4,5-trihydroxyphenyl)-ω-hydroxypoly(oxybutylene).

Example 3

Mannich Condensation Product of
α-(4-Hydroxyphenyl)-ω-hydroxypoly(oxybutylene)

To a flask equipped with a magnetic stirrer, thermometer, reflux condensor and nitrogen inlet was added the product from Example 2 (38.0 grams) and diethylene triamine (2.1 mL). The mixture was heated to 90° C. and formaldehyde (4.4 mL of a 37 weight percent solution in water) was added. The reaction was heated for sixteen hours at 90° C. and the temperature was then raised to 135° C. The reaction was maintained at 135° C. for two hours while sweeping out the water with a stream of nitrogen. The reaction was cooled to room temperature and yielded a brown oil. The oil was chromatographed on silica gel eluting with hexane/diethyl ether (1:1), followed by hexane/diethyl ether/methanol/isopropylamine (4:4:1.5:0.5) to yield 22 grams of the desired product as a brown oil. $^1$H NMR (CDCl$_3$, D$_2$O) δ 6.4–6.75 (m, 3H), 2.2–4.0 (m, 82H), 0.6–1.75 (m, 120H).

Example 4

Preparation of
α-(4-Hydroxyphenyl)-ω-benzyloxypoly(oxybutylene)

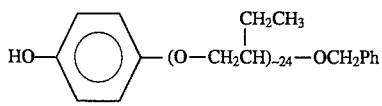

To a flask equipped with a magnetic stirrer, thermometer, reflux condenser and nitrogen inlet was added 0.8 grams of a 35 wt. % dispersion of potassium hydride in mineral oil. The oil was removed by trituration with anhydrous toluene.

The product from Example 2 (6.0 grams) was dissolved in 50 mL of anhydrous tetrahydrofuran and added dropwise to the potassium hydride. The reaction mixture was heated to reflux for 45 minutes and then cooled to room temperature. Benzyl chloride (0.36 mL) was added dropwise and the reaction was then heated to reflux for 12 hours, cooled to room temperature and quenched with 2 mL of isopropanol. The solvent was removed in vacuo and the residue dissolved in 200 mL of diethyl ether, washed with 5% aqueous hydrochloric acid, followed by saturated aqueous sodium chloride. The organic layer was dried over anhydrous magnesium sulfate, filtered and the solvents removed under vacuum. The oil was chromatographed on silica gel, eluting with hexane/ethyl acetate (7:3), to yield 3.8 grams of the desired product as a colorless oil. The product had an average of 24 oxybutylene units. $^1$H NMR (CDCl$_3$) δ 7.2–7.4 (m, 6H), 6.7 (s, 4H), 4.4–4.7 (m, 2H), 3.1–4.0 (m, 72H), 1.2–1.8 (m, 48H), 0.8 (t, 72H).

Similarly, by using the above procedures and the appropriate starting materials and reagents, the following compounds can by prepared:

α-(2-hydroxyphenyl)-ω-benzyloxypoly(oxybutylene);

α-(3-hydroxyphenyl)-ω-benzyloxypoly(oxybutylene);

α-(3,4-dihydroxyphenyl)-ω-benzyloxypoly(oxybutylene);

α-(3,5-di-t-butyl-4-hydroxyphenyl)-ω-benzyloxypoly(oxybutylene );

α-(4-hydroxy-3-methoxyphenyl)-ω-benzyloxy-poly(oxybutylene); and

α-[2-(4-hydroxyphenyl)ethyl]-ω-benzyloxypoly(oxybutylene).

Example 5

Mannich Condensation Product of
α-4-Hydroxyphenyl)-ω-benzyloxypolycoxybutylene)

To a flask equipped with a magnetic stirrer, thermometer, reflux condensor and nitrogen inlet was added a product prepared as in Example 4 (20.0 grams) and diethylene triamine (1.1 mL). The mixture was heated to 90° C. and formaldehyde (2.2 mL of a 37 weight percent solution in water) was added. The reaction was heated for sixteen hours at 90° C. and the temperature was then raised to 135° C. The reaction was maintained at 135° C. for two hours while sweeping out the water with a stream of nitrogen. The reaction was cooled to room temperature and yielded a brown oil. The oil was chromatographed on silica gel eluting with hexane/diethyl ether (1:1), followed by hexane/diethyl ether/methanol/isopropylamine (4:4:1.5:0.5) to yield 10 grams of the desired product as a brown oil. $^1$H NMR (CDCl$_3$, D$_2$O) δ 7.2–7.4 (m, 5H), 6.5–6.75 (m, 3H), 3.5–4.7 (m, 2H), 2.2–4.0 (m, 82H), 0.6–1.75 (m, 120H).

Example 6

Preparation of Methyl Adipoyl Chloride

To a flask equipped with a magnetic stirrer and drying tube was added 7.4 mL of mono-methyl adipate and 100 mL of anhydrous diethyl ether and then 21.8 mL of oxalyl chloride. The resulting mixture was stirred at room temperature for sixteen hours and then the solvent was removed in vacuo to yield 8.0 grams of the desired acid chloride.

Example 7

Preparation of
α-(4-Benzyloxyphenyl)-ω-(mono-methyladipolyoxyl) poly(oxybutylene)

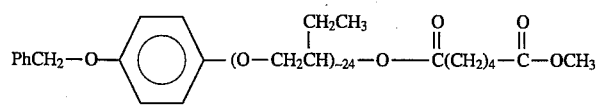

Methyl adipoyl chloride (3.57 grams) from Example 6 was combined with 42.48 grams of α-(4-benzyloxy-phenyl)-ω-hydroxypoly(oxybutylene) from Example 1 having an average of oxybutylene units and 200 mL of anhydrous toluene. Triethylamine (3.1 mL) and 4-dimethylaminopyridine (1.22 grams) were then added and the resulting mixture was heated to reflux under nitrogen for sixteen hours. The reaction was then cooled to room temperature and diluted with 400 mL of hexane. The organic layer was washed twice with water, twice with saturated aqueous sodium bicarbonate solution and once with saturated aqueous sodium chloride. The organic layer was then dried over anhydrous magnesium sulfate, filtered and the solvents removed in vacuo to yield 40.23 grams of the desired ester.

Example 8

Preparation of
α-(4-Hydroxyphenyl)-ω-(mono-methyladipoyloxy) poly(oxybutylene)

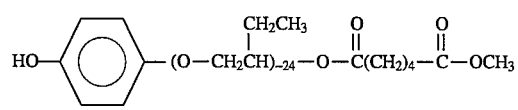

A solution of the ester from Example 7 (40.23 grams) in 100 mL of ethyl acetate and 100 mL of acetic acid containing 5.0 grams of 10% palladium on charcoal was hydrogenolyzed at 35–40 psi for sixteen hours on a Parr low-pressure hydrogenator. Filtration of the catalyst and removal of solvent in vacuo followed by azeotropic removal of residual acetic acid with toluene under vacuum yielded 36.3 grams of the desired product as a colorless oil. The product had an average of 24 oxybutylene units. IR (neat) 1742 cm$^{-1}$; $^1$H NMR (CDCl$_3$) δ 6.7 (s, 4H), 4.7–4.8 (m, 1H), 3.0–4.0 (m, 75H), 2.2(t, 4H), 0.6–1.7(m, 124H).

Example 9

Mannich Condensation Product of α-(4-Hydroxyphenyl)-ω-(monomethyladipoyloxy)poly(oxybutylene)

To a flask equipped with a magnetic stirrer, thermometer, reflux condensor and nitrogen inlet was added the product from Example 8 (15.0 grams) and diethylene triamine (0.9 mL). The mixture was heated to 90° C. and formaldehyde (0.7 mL of a 37 weight percent solution in water) was added. The reaction was heated for sixteen hours at 90° C. and the temperature was then raised to 135° C. The reaction was maintained at 135° C. for two hours while sweeping out the water with a stream of nitrogen. The reaction was cooled to room temperature and yielded a brown oil. The oil was chromatographed on silica gel eluting with hexane/diethyl ether (1:1), followed by hexane/diethyl ether/methanol/isopropylamine (4:4:1.5:0.5) to yield 9 grams of the desired product as a brown oil. IR (neat) 1742 cm$^{-1}$; $^1$H NMR (CDCl$_3$, D$_2$O) δ 6.4–6.75 (m, 3H), 4.75–4.9 (m, 1H), 2.3–4.0 (m, 84H), 2.25 (t, 4H), 0.6–1.75 (m, 124H).

Example 10

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I. (Reference to a compound by Example No. refers to the title composition for that Example.)

TABLE I

| Sample[1] | Intake Valve Deposit Weight (in milligrams) | | |
|---|---|---|---|
| | Run 1 | Run 2 | Average |
| Base Fuel | 297.0 | 280.4 | 288.7 |
| Example 3 | 0.4 | 10.0 | 5.2 |
| Example 5 | 0.0 | 0.0 | 0.0 |
| Example 9 | 49.7 | 60.3 | 55.0 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the outstanding reduction in intake valve deposits provided by the Mannich condensation product of the present fuel additive composition compared to the base fuel.

Obviously, many modifications and variations of the invention described hereinabove and below can be made without departing from the essence and scope thereof.

What is claimed is:

1. A composition prepared by the Mannich condensation of a compound of the formula:

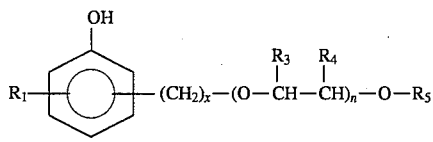

wherein R$_1$ is hydrogen, hydroxy, lower alkyl having 1 to 6 carbon atoms, or lower alkoxy having 1 to 6 carbon atoms;

R$_3$ and R$_4$ are each independently hydrogen or lower alkyl having 1 to 6 carbon atoms;

R$_5$ is hydrogen, alkyl having 1 to 30 carbon atoms, phenyl, aralkyl or alkaryl having 7 to 36 carbon atoms, or an acyl group having the formula:

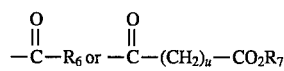

wherein R$_6$ is alkyl having 1 to 30 carbon atoms, phenyl, or aralkyl or alkaryl having 7 to 36 carbon atoms; R$_7$ is alkyl having 1 to about 10 carbon atoms; and u is an integer from 1 to 10;

n is an integer from 5 to 100; and x is an integer from 0 to 10;

with an aldehyde having the formula HR$_2$C(O), wherein R$_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

2. The composition according to claim 1, wherein n is an integer ranging from 10 to 50.

3. The composition according to claim 2, wherein n is an integer ranging from 15 to 30.

4. The composition according to claim 2, wherein R$_1$ is hydrogen, hydroxy, or lower alkyl having 1 to 4 carbon atoms; and said nitrogen base is an alkylene diamine or polyalkylene polyamine..

5. The composition according to claim 4, wherein R$_5$ is hydrogen, alkyl having 1 to 24 carbon atoms, or alkylphenyl or phenylalkyl having an alkyl group containing 1 to 24 carbon atoms.

6. The composition according to claim 5, wherein R$_1$ is hydrogen or hydroxy, and said nitrogen base is an ethylene diamine or polyethylene polyamine or a propylene diamine or polypropylene polyamine.

7. The composition according to claim 6, wherein R$_5$ is hydrogen, alkyl having 4 to 12 carbon atoms, or alkylphenyl or phenylalkyl having an alkyl group containing 1 to 12 carbon atoms.

8. The composition according to claim 7, wherein one of $R_3$ and $R_4$ is lower alkyl having 1 to 3 carbon atoms and the other is hydrogen.

9. The composition according to claim 8, wherein one of $R_3$ and $R_4$ is methyl or ethyl and the other is hydrogen.

10. The composition according to claim 9, wherein x is 0, 1 or 2.

11. The composition according to claim 10, wherein $R_1$ is hydrogen, $R_5$ is alkylphenyl or phenylalkyl having an alkyl group containing 1 to 12 carbon atoms, x is 0, and said nitrogen base is ethylene diamine or diethylene triamine.

12. A compound of the formula:

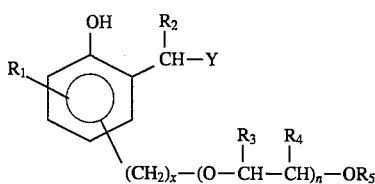

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

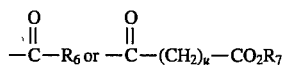

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10; and

Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

13. The compound according to claim 12, wherein n is an integer ranging from 10 to 50.

14. The compound according to claim 13, wherein n is an integer ranging from 15 to 30.

15. The compound according to claim 13, wherein $R_1$ is hydrogen, hydroxy, or lower alkyl having 1 to 4 carbon atoms; and Y is an alkylene diamine or polyalkylene polyamine radical.

16. The compound according to claim 15, wherein $R_5$ is hydrogen, alkyl having 1 to 24 carbon atoms, or alkylphenyl or phenylalkyl having an alkyl group containing 1 to 24 carbon atoms.

17. The compound according to claim 16, wherein $R_1$ is hydrogen or hydroxy, and Y is an ethylene diamine or polyethylene polyamine radical or a propylene diamine or polypropylene polyamine radical.

18. The compound according to claim 17, wherein $R_5$ is hydrogen, alkyl having 4 to 12 carbon atoms, or alkylphenyl or phenylalkyl having an alkyl group containing 1 to 12 carbon atoms.

19. The compound according to claim 18, wherein one of $R_3$ and $R_4$ is lower alkyl having 1 to 3 carbon atoms and the other is hydrogen.

20. The compound according to claim 19, wherein one of $R_3$ and $R_4$ is methyl or ethyl and the other is hydrogen.

21. The compound according to claim 20, wherein x is 0, 1 or 2.

22. The compound according to claim 21, wherein $R_1$ is hydrogen, $R_5$ is alkylphenyl or phenylalkyl having an alkyl group containing 1 to 12 carbon atoms, x is 0, and Y is an ethylene diamine radical or a diethylene triamine radical.

23. A fuel composition comprising a major amount of hydrocarbons boiling in the gasoline or diesel range and an effective deposit-controlling amount of a composition prepared by the Mannich condensation of a compound of the formula:

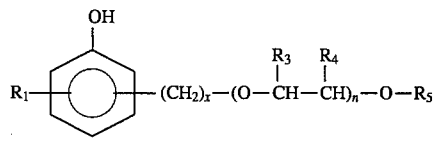

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

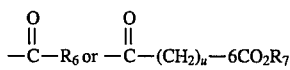

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10;

with an aldehyde having the formula $HR_2C(O)$, wherein $R_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

24. The fuel composition according to claim 23, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 1 to 24 carbon atoms, or alkylphenyl or phenylalkyl having an alkyl group containing 1 to 24 carbon atoms; n is 15 to 30; x is 0, 1 or 2; and said nitrogen base is an alkylene diamine or polyalkylene polyamine.

25. The fuel composition according to claim 24, wherein $R_1$ is hydrogen or hydroxy; $R_5$ is hydrogen, alkyl having 1 to 12 carbon atoms, or alkylphenyl or phenylalkyl having an alkyl group containing 1 to 12 carbon atoms; x is 0; and said nitrogen base is an ethylene diamine or polyethylene polyamine or a propylene diamine or polypropylene polyamine.

26. The fuel composition according to claim 25, wherein $R_1$ is hydrogen, $R_5$ is alkylphenyl or phenylalkyl having an alkyl group containing 1 to 12 carbon atoms, and said nitrogen base is ethylene diamine or diethylene triamine.

27. A fuel composition comprising a major amount of hydrocarbons boiling in the gasoline or diesel range and an effective deposit-controlling amount of a compound of the formula:

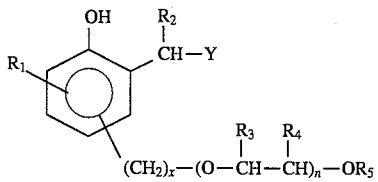

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

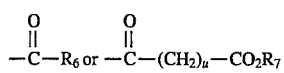

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10; and

Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

28. The fuel composition according to claim 27, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 1 to 24 carbon atoms, or alkylphenyl or phenylalkyl having an alkyl group containing 1 to 24 carbon atoms; n is 15 to 30; x is 0, 1 or 2; and Y is an alkylene diamine or polyalkylene polyamine radical.

29. The fuel composition according to claim 28, wherein $R_1$ is hydrogen or hydroxy; $R_5$ is hydrogen, alkyl having 4 to 12 carbon atoms, or alkylphenyl or phenylalkyl having an alkyl group containing 1 to 12 carbon atoms; x is 0; and Y is an alkylene diamine or polyalkylene polyamine radical.

30. The fuel composition according to claim 29, wherein $R_1$ is hydrogen, $R_5$ is alkylphenyl or phenylalkyl having an alkyl group containing 1 to 12 carbon atoms, and Y is an ethylene diamine radical or a diethylene triamine radical.

31. A fuel concentrate comprising an inert stable oleophilic organic solvent boiling in the range of from about 150° F. to 400° F. and from about 10 to about 70 weight percent of a composition prepared by the Mannich condensation of a compound of the formula:

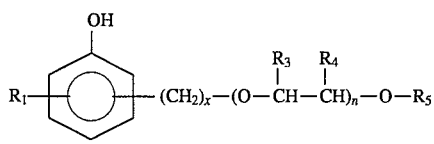

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

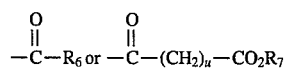

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer of from 1 to 10;

n is an integer from 5 to 100; and x is an integer from 0 to 10;

with an aldehyde having the formula $HR_2C(O)$, wherein $R_3$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

32. The fuel concentrate according to claim 31, wherein $R_1$ is hydrogen, hydroxy, or lower alkyl having 1 to 4 carbon atoms; one of R3 and R4 is hydrogen and the other is methyl or ethyl; $R_5$ is hydrogen, alkyl having 1 to 24 carbon atoms, or alkylphenyl or phenylalkyl having an alkyl group containing 1 to 24 carbon atoms; n is 15 to 30; x is 0, 1 or 2; and said nitrogen base is an alkylene diamine or polyalkylene polyamine.

33. The fuel concentrate according to claim 32, wherein $R_1$ is hydrogen or hydroxy; $R_5$ is hydrogen, alkyl having 4 to 12 carbon atoms, or alkylphenyl or phenylalkyl having an alkyl group containing 1 to 12 carbon atoms; x is 0; and said nitrogen base is an ethylene diamine or polyethylene. polyamine or a propylene diamine or polypropylene polyamine.

34. The fuel concentrate according to claim 33, wherein $R_1$ is hydrogen, $R_5$ is alkylphenyl or phenylalkyl having an alkyl group containing 1 to 12 carbon atoms, and said nitrogen base is ethylene diamine or diethylene triamine.

35. A fuel concentrate comprising an inert stable oleophilic organic solvent boiling in the range of from about 150° F. to 400° F. and from about 10 to about 70 weight percent of a compound of the formula:

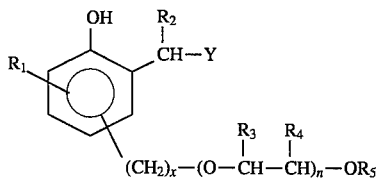

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

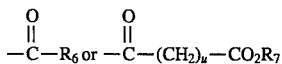

wherein $R_6$ is alkyl having 1 to 30 carbon atoms, phenyl, or aralkyl or alkaryl having 7 to 36 carbon atoms; $R_7$ is alkyl having 1 to about 10 carbon atoms; and u is an integer from 1 to 10;

n is an integer from 5 to 100; and x is an integer from 0 to 10; and

Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

36. The fuel concentrate according to claim 35, wherein $R_1$ is hydrogen, hydroxy, or lower alkyl having 1 to 4 carbon atoms; one of R3 and P-4 is hydrogen and the other is methyl or ethyl; $R_5$ is hydrogen, alkyl having 1 to 24 carbon atoms, or alkylphenyl or phenylalkyl having an alkyl group containing 1 to 24 carbon atoms; n is 15 to 30; x is 0, 1 or 2; and Y is an alkylene diamine or polyalkylene polyamine radical.

37. The fuel concentrate according to claim 36, wherein $R_1$ is hydrogen or hydroxy; $R_5$ is hydrogen, alkyl having 4 to 12 carbon atoms, or alkylphenyl or phenylalkyl having an alkyl group containing 1 to 12 carbon atoms; x is 0; and Y is an ethylene diamine. Or polyethylene polyamine radical or a propylene diamine or polypropylene polyamine radical.

38. The fuel concentrate according to claim 37, wherein $R_1$ is hydrogen, $R_5$ is alkylphenyl or phenylalkyl having an alkyl group containing 1 to 12 carbon atoms, and Y is an ethylene diamine radical or a diethylene triamine radical.

* * * * *